United States Patent
Michihata

(10) Patent No.: US 12,213,643 B2
(45) Date of Patent: Feb. 4, 2025

(54) LEARNING DEVICE AND MEDICAL IMAGE PROCESSING DEVICE

(71) Applicant: Sony Olympus Medical Solutions Inc., Tokyo (JP)

(72) Inventor: Taihei Michihata, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 23 days.

(21) Appl. No.: 17/798,570

(22) PCT Filed: Feb. 9, 2021

(86) PCT No.: PCT/JP2021/004847
§ 371 (c)(1),
(2) Date: Aug. 10, 2022

(87) PCT Pub. No.: WO2021/166749
PCT Pub. Date: Aug. 26, 2021

(65) Prior Publication Data
US 2023/0112628 A1    Apr. 13, 2023

(30) Foreign Application Priority Data
Feb. 18, 2020   (JP) .................. 2020-024944

(51) Int. Cl.
*A61B 1/005* (2006.01)
*A61B 1/00* (2006.01)
(Continued)

(52) U.S. Cl.
CPC ........ *A61B 1/000096* (2022.02); *A61B 1/043* (2013.01); *A61B 1/0638* (2013.01); *A61B 1/0655* (2022.02)

(58) Field of Classification Search
None
See application file for complete search history.

(56) References Cited

U.S. PATENT DOCUMENTS

| 2017/0083791 A1 | 3/2017 | Shiratani |
| 2017/0154234 A1 | 6/2017 | Tanaka |
| (Continued) | | |

FOREIGN PATENT DOCUMENTS

| JP | 2015-29841 A | 2/2015 |
| JP | 2016209542 A | 12/2016 |
| (Continued) | | |

OTHER PUBLICATIONS

International Search Report and Written Opinion mailed on Apr. 6, 2021, received for PCT Application PCT/JP2021/004847, filed on Feb. 9, 2021, 9 pages including English Translation.
(Continued)

*Primary Examiner* — Samuel D Fereja
(74) *Attorney, Agent, or Firm* — XSENSUS LLP

(57) ABSTRACT

A learning device 3 includes: a training image acquisition unit 321 that acquires training images in which a first training image acquired by capturing light from a subject irradiated with light in a first wavelength band and a second training image acquired by capturing light from the subject irradiated with light in a second wavelength band different from the first wavelength band are paired; a singular area specification unit 322 that specifies a singular area in the second training image; a first feature data extraction unit 323 that extracts feature data of a singular-corresponding area at a pixel position corresponding to the singular area in the first training image; and a singular-corresponding area learning unit 324 that generates a learning model by performing machine learning on the singular-corresponding area based on the feature data.

13 Claims, 8 Drawing Sheets

(51) Int. Cl.
   *A61B 1/04*    (2006.01)
   *A61B 1/05*    (2006.01)
   *A61B 1/06*    (2006.01)
   *A61B 1/07*    (2006.01)

(56) References Cited

U.S. PATENT DOCUMENTS

2020/0051264 A1    2/2020  Mishima
2023/0016855 A1*   1/2023  Endo ................ A61B 1/000096

FOREIGN PATENT DOCUMENTS

| KR | 101463354 B1 | 11/2014 |
| WO | WO-2018225448 A1 | 12/2018 |
| WO | WO-2019230302 A1 | 12/2019 |
| WO | 2020/003991 A1 | 1/2020 |
| WO | 2020/022027 A1 | 1/2020 |
| WO | WO-2020017213 A1 * | 1/2020 |

OTHER PUBLICATIONS

Ota et al., "Extraction of Tongue Coating by Machine Learning Using Texture and Color Features", Proceedings of JAMIT Annual Meeting, Jul. 27, 2017, 5 pages including English Abstract.
Takehiro Ota, "Fur-Coating-of-Tongue Extraction by Machine Learning Using Outside Binary Name, Texture, and Color Feature", 36th Japanese Society of Medical Imaging and Technology Convention Proceedings, Jul. 27, 2017, p. 332-335.

* cited by examiner

LEARNING DEVICE AND MEDICAL IMAGE PROCESSING DEVICE

CROSS-REFERENCE TO RELATED APPLICATIONS

The present application is based on PCT filing PCT/JP2021/004847, filed Feb. 9, 2021, which claims priority to Japanese Application No. 2020-024944, filed Feb. 18, 2020, the entire contents of each are incorporated herein by reference.

FIELD

The present disclosure relates to a learning device and a medical image processing device.

BACKGROUND

Conventionally, a rigid endoscope system that administers a fluorescent substance such as indocyanine green into a living body, emits excitation light to excite the fluorescent substance to an observation target, and performs fluorescent observation of a lesion where the fluorescent substance is accumulated (see, for example, Patent Literature 1) has been known.

In the rigid endoscope system described in Patent Literature 1, the following first and second captured images are acquired, and a superimposed image is generated by superimposition of corresponding pixels of the first and second captured images.

The first captured image is an image captured in the following manner. That is, normal light that is white light is emitted to the observation target, and the normal light reflected by the observation target is captured by an imaging element.

The second captured image is an image captured in the following manner. That is, the excitation light that excites the fluorescent substance such as indocyanine green is emitted to the observation target, and fluorescence from the observation target excited by the excitation light is captured by a high-sensitivity imaging element.

CITATION LIST

Patent Literature

Patent Literature 1: JP 2015-29841 A

SUMMARY

Technical Problem

However, in the rigid endoscope system described in Patent Literature 1, it is necessary to administer a fluorescent substance such as indocyanine green into a living body in order to observe a lesion (area of fluorescence emitted from an observation target (hereinafter, referred to as fluorescent area)). For example, when the fluorescent area can be estimated from the first captured image without the administration, convenience can be improved.

The present disclosure has been provided in view of the forgoing and is to provide a learning device and a medical image processing device capable of improving convenience.

Solution to Problem

To solve the above-described problem and achieve the object, a learning device according to the present disclosure includes: a training image acquisition unit configured to acquire training images in which a first training image acquired by capturing light from a subject irradiated with light in a first wavelength band and a second training image acquired by capturing light from the subject irradiated with light in a second wavelength band different from the first wavelength band are paired; a singular area specification unit configured to specify a singular area in the second training image; a first feature data extraction unit configured to extract feature data of a singular-corresponding area at a pixel position, the pixel position corresponding to the singular area in the first training image; and a singular-corresponding area learning unit configured to generate a learning model by performing machine learning on the singular-corresponding area based on the feature data.

Moreover, in the above-described learning device according to the present disclosure, the subject emits fluorescence by being irradiated with excitation light in the second wavelength band, the second training image is acquired by capturing the fluorescence from the subject irradiated with the excitation light, and the singular area specification unit is configured to specify, as the singular area, an area in which intensity of a component of the fluorescence is equal to or higher than a specific threshold in the second training image.

Moreover, in the above-described learning device according to the present disclosure, the singular area specification unit is configured to specify, as the singular area, an area in which a pixel level is equal to or higher than a specific threshold in the second training image.

Moreover, in the above-described learning device according to the present disclosure, the singular area specification unit is configured to specify, as the singular area, each of a first singular area in which the pixel level is within a first range and a second singular area in which the pixel level is within a second range higher than the first range, the first feature data extraction unit is configured to extract feature data of each of a first singular-corresponding area, which is the singular-corresponding area in the first training image and is at a pixel position corresponding to the first singular area, and a second singular-corresponding area which is the singular-corresponding area in the first training image and is at a pixel position corresponding to the second singular area, and the singular-corresponding area learning unit is configured to perform machine learning on each of the first singular-corresponding area and the second singular-corresponding area based on the feature data.

Moreover, in the above-described learning device according to the present disclosure, the feature data includes feature data related to at least one of color and luminance, and the singular-corresponding area learning unit is configured to make a weight of the feature data related to a blue color component lower than a weight of the feature data related to another color component when performing the machine learning on the singular-correspondence area and generating a learning model.

Moreover, in the above-described learning device according to the present disclosure, the light in the first wavelength band is emitted in a first period of the first period and a second period that are alternately repeated, and the light in the second wavelength band is emitted in the second period.

A medical image processing device according to the present disclosure includes: a captured image acquisition unit configured to acquire a captured image acquired by capturing light from an observation target irradiated with light in a first wavelength band; a second feature data extraction unit configured to extract feature data of each area of the captured image; and a singular-corresponding area specification unit configured to specify a singular-corresponding area in the captured image by using a learning model constructed by machine learning based on the feature data, wherein the learning model is generated by the machine learning on the singular-corresponding area by utilization of training images, in which a first training image acquired by capturing light from a subject irradiated with the light in the first wavelength band and a second training image acquired by capturing light from the subject irradiated with light in a second wavelength band different from the first wavelength band are paired, based on the feature data of the singular-corresponding area at a pixel position, the pixel position corresponding to a singular area in the second training image, in the first training image.

Moreover, in the above-described medical image processing device according to the present disclosure, the subject emits fluorescence by being irradiated with excitation light in the second wavelength band, the second training image is acquired by capturing the fluorescence from the subject irradiated with the excitation light, and the singular area is an area in which intensity of a component of the fluorescence is equal to or higher than a specific threshold in the second training image.

Moreover, in the above-described medical image processing device according to the present disclosure, the singular area is an area in which a pixel level is equal to or larger than a specific threshold in the second training image.

Moreover, in the above-described medical image processing device according to the present disclosure, the singular area includes a first singular area in which the pixel level is within a first range, and a second singular area in which the pixel level is within a second range higher than the first range, and the learning model is generated by machine learning on each of a first singular-corresponding area, which is the singular-corresponding area in the first training image and is at a pixel position corresponding to the first singular area, and a second singular-corresponding area, which is the singular-corresponding area in the first training image and is at a pixel position corresponding to the second singular area, based on the feature data of the first singular-corresponding area and the second singular-corresponding area.

Moreover, in the above-described medical image processing device according to the present disclosure, the feature data includes feature data related to at least one of color and luminance, and the learning model is generated by machine learning on the singular-corresponding area in a state in which a weight of the feature data related to a blue color component is made lower than a weight of the feature data related to another color component.

Moreover, in the above-described medical image processing device according to the present disclosure, the light in the first wavelength band is emitted in a first period of the first period and a second period that are alternately repeated, and the light in the second wavelength band is emitted in the second period.

Moreover, the above-described medical image processing device according to the present disclosure further includes a display controller configured to generate a display image in which the singular-corresponding area is displayed in a manner of being distinguished from another area in the captured image.

Advantageous Effects of Invention

The learning device and the medical image processing device according to the present disclosure can improve convenience.

DESCRIPTION OF EMBODIMENTS

Figure 1:
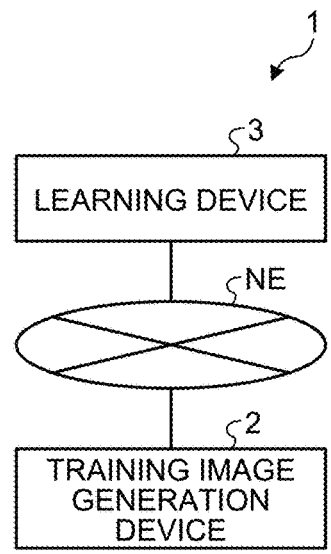
FIG. 1 is a view illustrating a configuration of a learning system according to an embodiment.

In the following, modes for carrying out the present disclosure (hereinafter, embodiment) will be described with reference to the drawings. Note that the present disclosure is not limited to the embodiments described in the following. Furthermore, the same reference sign is assigned to the same parts in the drawings.

[1. Schematic Configuration of a Learning System]

FIG. 1 is a view illustrating a configuration of a learning system 1 according to the present embodiment.

The learning system 1 is a system that generates a learning model used to estimate a fluorescent area (singular area) where fluorescence is emitted when near-infrared excitation light is emitted to an observation target. As illustrated in FIG. 1, this learning system 1 includes a training image generation device 2 and a learning device 3. Then, these training image generation device 2 and learning device 3 perform wired or wireless communication via a network NE (FIG. 1).

Note that although only one training image generation device 2 is illustrated in FIG. 1, the number of training image generation devices 2 is not limited to one and may be plural.

[2. Configuration of the Training Image Generation Device]

First, the configuration of the training image generation device 2 will be described.

Figure 2:
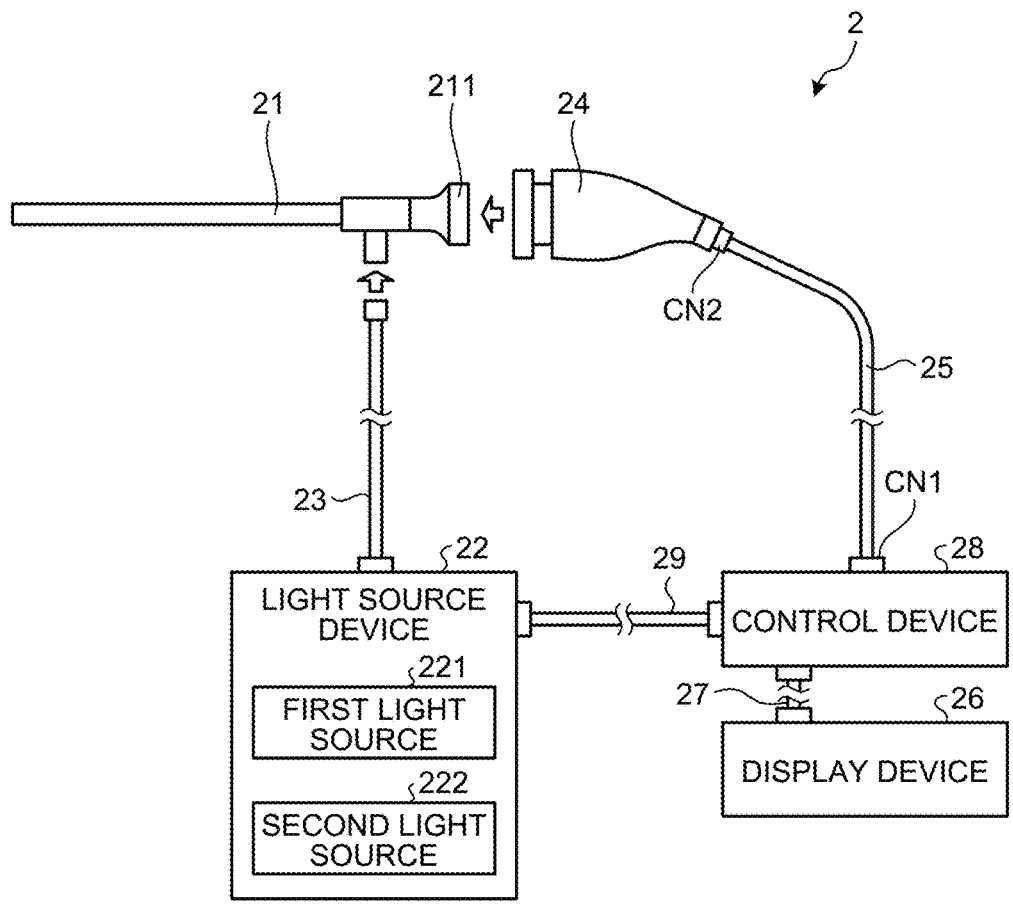
FIG. 2 is a view illustrating a configuration of a training image generation device.

FIG. 2 is a view illustrating the configuration of the training image generation device 2.

The training image generation device 2 is a device that generates a training image used for machine learning in the learning device 3. As illustrated in FIG. 2, this training image generation device 2 includes an insertion unit 21, a light source device 22, a light guide 23, a camera head 24, a first transmission cable 25, a display device 26, a second transmission cable 27, a control device 28, and a third transmission cable 29.

The insertion unit 21 is a rigid endoscope. That is, the insertion unit 21 has an elongated shape that is entirely rigid or that is partially flexible and partially rigid, and is inserted into a living body. In this insertion unit 21, an optical system that includes one or a plurality of lenses and that collects light from the inside of the living body (subject) is provided.

One end of the light guide 23 is connected to the light source device 22, and light emitted to the inside of the living body is supplied therefrom to the one end of the light guide 23 under the control of the control device 28. As illustrated in FIG. 2, this light source device 22 includes a first light source 221 and a second light source 222.

The first light source 221 emits normal light in a first wavelength band. In the present embodiment, the first light source 221 includes a light emitting diode (LED) that emits white light.

The second light source 222 emits excitation light in a second wavelength band different from the first wavelength band. In the present embodiment, a semiconductor laser that emits near-infrared excitation light in a near-infrared wavelength band is included. The near-infrared excitation light is excitation light that excites a fluorescent substance such as indocyanine green. Furthermore, when excited by the near-infrared excitation light, the fluorescent substance such as indocyanine green emits fluorescence having a central wavelength on a longer wavelength side of a central wavelength of the wavelength band of the near-infrared excitation light. Note that the wavelength band of the near-infrared excitation light and the wavelength band of the fluorescence may be set in such a manner as to partially overlap or may be set in such a manner as not to overlap at all.

Then, between alternately repeated first and second periods, the first light source 221 is driven in the light source device 22 in the first period under the control of the control device 28. That is, the light source device 22 emits the normal light (white light) in the first period. Furthermore, the second light source 222 is driven in the light source device 22 in the second period under the control of the control device 28. That is, the light source device 22 emits the near-infrared excitation light in the second period.

Note that although the light source device 22 is configured separately from the control device 28 in the present embodiment, this is not a limitation, and a configuration of being provided inside the control device 28 may be employed.

One end of the light guide 23 is detachably connected to the light source device 22, and the other end thereof is detachably connected to the insertion unit 21. Then, the light guide 23 transmits the light (normal light or near-infrared excitation light) supplied from the light source device 22 from the one end to the other end, and supplies the light to the insertion unit 21. In a case where the normal light (white light) is emitted to the inside of the living body, the normal light reflected inside the living body is collected by the optical system in the insertion unit 21. Note that the normal light collected by the optical system in the insertion unit 21 is referred to as a first subject image in the following, for convenience of description. In addition, in a case where the near-infrared excitation light is emitted to the inside of the living body, the near-infrared excitation light reflected inside the living body, and fluorescence emitted from the excited fluorescent substance such as indocyanine green accumulated at a lesion in the living body are collected by the optical system in the insertion unit 21. Note that fluorescence transmitted through an excitation light cut-off filter 242a (described later) after the collection of the near-infrared excitation light and the fluorescence by the optical system in the insertion unit 21 is referred to as a second subject image in the following, for convenience of description.

The camera head 24 is detachably connected to a proximal end (eyepiece 211 (FIG. 2)) of the insertion unit 21. Then, under the control of the control device 28, the camera head 24 captures the first subject image (normal light) and the second subject image (fluorescence), and outputs an image signal (RAW signal) acquired by the imaging. The image signal is, for example, an image signal of 4K or higher.

Note that a detailed configuration of the camera head 24 will be described in "2-1. Configuration of the camera head" described later.

One end of the first transmission cable 25 is detachably connected to the control device 28 via a connector CN1 (FIG. 2), and the other end thereof is detachably connected to the camera head 24 via a connector CN2 (FIG. 2). Then, the first transmission cable 25 transmits the image signal and the like output from the camera head 24 to the control device 28, and also transmits a control signal, synchronization signal, clock, electric power, and the like output from the control device 28 to the camera head 24.

Note that in the transmission of the image signal and the like from the camera head 24 to the control device 28 through the first transmission cable 25, the image signal and the like may be transmitted as an optical signal or may be transmitted as an electric signal. The same applies to transmission of the control signal, synchronization signal, and clock from the control device 28 to the camera head 24 through the first transmission cable 25.

The display device 26 includes a display using liquid crystal, organic electro luminescence (EL), or the like, and displays an image based on a video signal from the control device 28 under the control of the control device 28.

One end of the second transmission cable 27 is detachably connected to the display device 26, and the other end thereof is detachably connected to the control device 28. Then, the second transmission cable 27 transmits the video signal processed by the control device 28 to the display device 26.

The control device 28 includes a central processing unit (CPU), a field-programmable gate array (FPGA), or the like, and comprehensively controls operations of the light source device 22, the camera head 24, and the display device 26.

Note that a detailed configuration of the control device 28 will be described in "2-2. Configuration of the control device" described later.

One end of the third transmission cable 29 is detachably connected to the light source device 22, and the other end thereof is detachably connected to the control device 28. Then, the third transmission cable 29 transmits the control signal from the control device 28 to the light source device 22.

[2-1. Configuration of the Camera Head]

Next, the configuration of the camera head 24 will be described.

Figure 3:
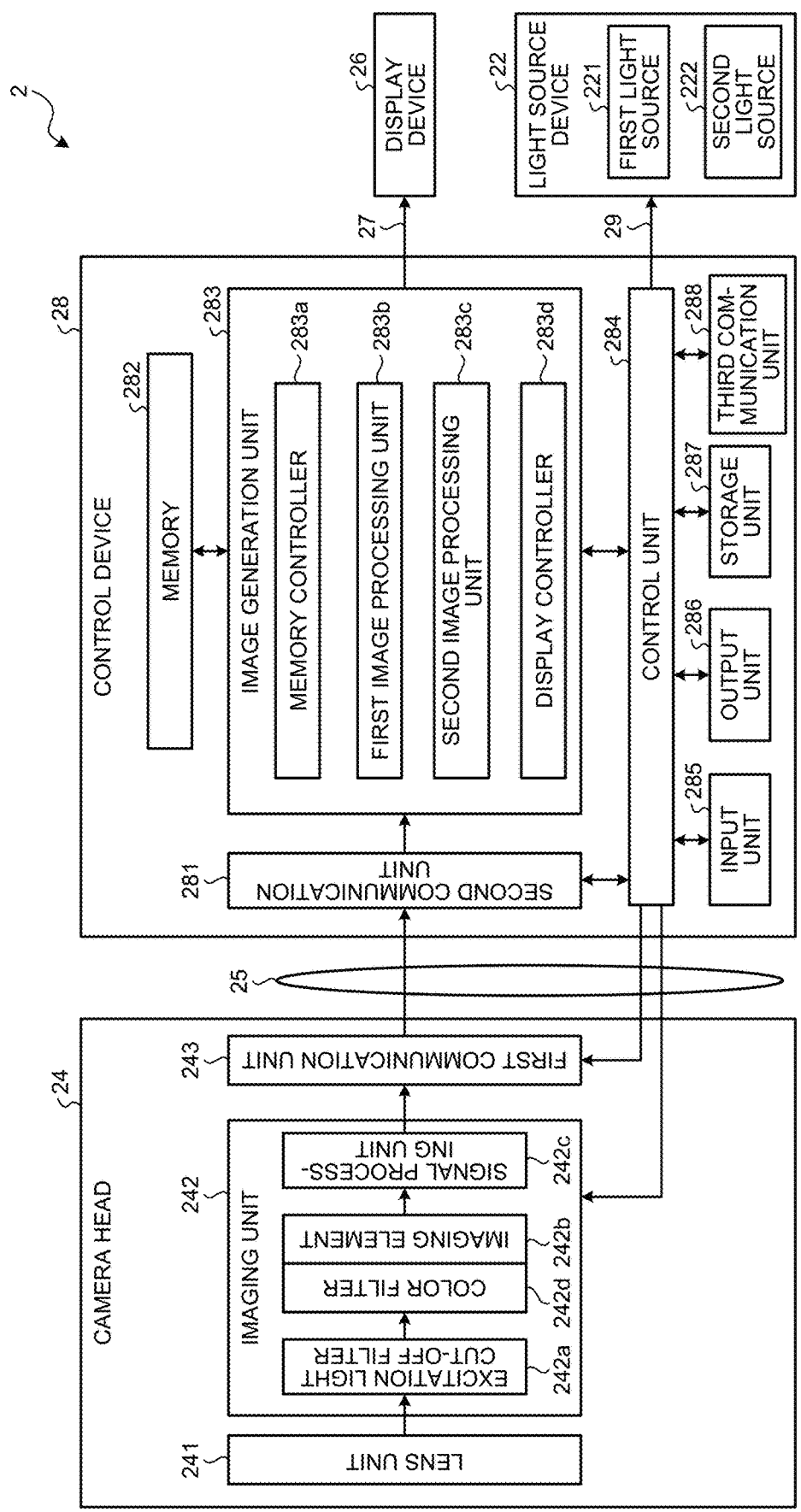
FIG. 3 is a view illustrating configurations of a camera head and a control device.

FIG. 3 is a view illustrating configurations of the camera head 24 and the control device 28.

Note that the connectors CN1 and CN2 between the control device 28 and the camera head 24 and the first transmission cable 25, connectors between the control device 28 and the display device 26 and the second transmission cable 27, and connectors between the control device 28 and the light source device 22 and the third transmission cable 29 are omitted in FIG. 3, for convenience of description.

As illustrated in FIG. 3, the camera head 24 includes a lens unit 241, an imaging unit 242, and a first communication unit 243.

The lens unit 241 includes one or a plurality of lenses, and forms the first subject image (normal light) and the second subject image (fluorescence) on an imaging surface of the imaging unit 242 (imaging element 242b).

The imaging unit 242 captures the inside of the living body under the control of the control device 28. As illustrated in FIG. 3, this imaging unit 242 includes an excitation light cut-off filter 242a, an imaging element 242b, and a signal processing unit 242c.

The excitation light cut-off filter 242a is provided between the lens unit 241 and the imaging element 242b, and includes a band-stop filter that removes a specific wavelength band. That is, the excitation light cut-off filter 242a is arranged on an optical path of the near-infrared excitation light, which is reflected inside the living body, from the inside of the living body to the imaging element 242b. Note that the wavelength band that is cut (removed) by the excitation light cut-off filter 242a is referred to as a cut band, a wavelength band that is on a short wavelength side of the cut band and passes through the excitation light cut-off filter 242a is referred to as a short wave-side transmission band, and a wavelength band that is on a long wavelength side of the cut band and passes through the excitation light cut-off filter 242a is referred to as a long wave-side transmission band in the following, for convenience of description.

Here, the cut band includes at least a part of the wavelength band of the near-infrared excitation light. In the present embodiment, the cut band includes the entire wavelength band of the near-infrared excitation light. In addition, the long wave-side transmission band includes the entire wavelength band of the fluorescence. Furthermore, the short wave-side transmission band includes the entire wavelength band of the normal light (white light).

That is, the excitation light cut-off filter 242a transmits the first subject image (normal light (white light)) from the lens unit 241 toward the imaging element 242b. On the other hand, with respect to the near-infrared excitation light and the fluorescence from the lens unit 241 toward the imaging element 242b, the excitation light cut-off filter 242a cuts (removes) the near-infrared excitation light and transmits the fluorescence (second subject image).

The imaging element 242b includes a charge coupled device (CCD), a complementary metal oxide semiconductor (CMOS), or the like that receives light transmitted through the excitation light cut-off filter 242a and that performs conversion thereof into an electric signal (analog signal).

Here, the imaging surface (light receiving surface) of the imaging element 242b is provided with a color filter 242d (FIG. 3) in which three filter groups grouped according to wavelength bands of transmitted light (red (R), green (G), and blue (B)) are arrayed in a predetermined format (such as Bayer array).

Specifically, the color filter 242d includes an R filter group that mainly transmits light in an R wavelength band, a B filter group that mainly transmits light in a B wavelength band, a first G filter group (arrayed in the same column as the R filter group) that mainly transmits light in the G wavelength band, and a second G filter group (arrayed in the same column as the B filter group) that mainly transmits the light in the G wavelength band. Note that the first and second G filter groups are collectively referred to as a G filter group in the following, for convenience of description.

Here, each of the R, G, and B filter groups also transmits the fluorescence. Also, the imaging element 242b has sensitivity not only to the light in the R, G, and B wavelength bands but also to light in the wavelength band of the fluorescence.

Then, the imaging element 242b performs imaging in every first and second periods that are alternately repeated in synchronization with light emission timing of the light source device 22 under the control of the control device 28. Hereinafter, for convenience of description, an image generated by capturing the first subject image (normal light) by the imaging element 242b in the first period is referred to as a first training image, and an image generated by capturing the second subject image (fluorescence) by the imaging element 242b in the second period is referred to as a second training image. In addition, the first and second training images are collectively referred to as a training image.

The signal processing unit 242c performs signal processing on the training image (analog signal) generated by the imaging element 242b and outputs the training image (RAW signal (digital signal)).

The first communication unit 243 functions as a transmitter that transmits the training image (RAW signal (digital signal)) output from the imaging unit 242 to the control device 28 through the first transmission cable 25. This first communication unit 243 includes, for example, a high-speed serial interface that performs communication of the training image at a transmission rate equal to or higher than 1 Gbps with the control device 28 through the first transmission cable 25.

[2-2. Configuration of the Control Device]

Next, the configuration of the control device 28 will be described with reference to FIG. 3.

As illustrated in FIG. 3, the control device 28 includes a second communication unit 281, a memory 282, an image generation unit 283, a control unit 284, an input unit 285, an output unit 286, a storage unit 287, and a third communication unit 288.

The second communication unit 281 functions as a receiver that receives the training image (RAW signal (digital signal)) output from the camera head 24 (first communication unit 243) through the first transmission cable 25. This second communication unit 281 includes, for example, a high-speed serial interface that performs communication of the training image with the first communication unit 243 at the transmission rate equal to or higher than 1 Gbps.

The memory 282 includes, for example, a dynamic random access memory (DRAM) or the like. This memory 282 can temporarily store a plurality of frames of training images sequentially output from the camera head 24 (first communication unit 243).

The image generation unit 283 processes the training images (RAW signals (digital signals)) sequentially output from the camera head 24 (first communication unit 243) and received by the second communication unit 281 under the control of the control unit 284. As illustrated in FIG. 3, this image generation unit 283 includes a memory controller 283a, a first image processing unit 283b, a second image processing unit 283c, and a display controller 283d.

The memory controller 283a controls writing and reading of the training images to and from the memory 282. More specifically, the memory controller 283a sequentially writes, in the memory 282, the training images (first and second training images) sequentially output from the camera head 24 (first communication unit 243) and received by the second communication unit 281. In addition, the memory controller 283a reads the first training image from the memory 282 at certain timing, and causes the first image processing unit 283b to input the read first training image. Furthermore, the memory controller 283a reads the second training image from the memory 282 at certain timing, and causes the second image processing unit 283c to input the read second training image.

The first image processing unit 283b executes first image processing on the input first training image (RAW signal (digital signal)).

Examples of the first image processing include optical black subtraction processing, white balance adjustment processing, demosaic processing, color correction processing, gamma correction processing, and YC processing of converting an RGB signal (first training image) into a luminance signal and a color difference signal (Y and $C_B/C_R$ signals).

The second image processing unit 283c executes second image processing different from the first image processing on the input second training image (RAW signal (digital signal)).

Examples of the second image processing include processing of generating only a luminance signal (Y signal) from the input second training image (RAW signal (digital signal)).

The display controller 283d generates a video signal for a display which signal is to display at least one of the first training image on which the first image processing is executed by the first image processing unit 283b and the second training image on which the second image processing is executed by the second image processing unit 283c. Then, the display controller 283d outputs the video signal to the display device 26 through the second transmission cable 27.

The control unit 284 includes, for example, a CPU, an FPGA, or the like, and controls the operations of the light source device 22, the camera head 24, and the display device 26 and controls the operation of the entire control device 28 by outputting a control signal through the first to third transmission cables 25, 27, and 29.

Note that a part of the function of the control unit 284 will be described in "3. Operation of the training image generation device" described later.

The input unit 285 includes operation devices such as a mouse, a keyboard, and a touch panel, and receives user operation by a user such as a doctor. Then, the input unit 285 outputs an operation signal corresponding to the user operation to the control unit 284.

The output unit 286 includes a speaker, a printer, or the like, and outputs various kinds of information.

The storage unit 287 stores a program executed by the control unit 284, information necessary for processing by the control unit 284, and the like.

The third communication unit 288 transmits/receives information to/from the learning device 3 via the network NE under the control of the control unit 284.

[3. Operation of the Training Image Generation Device]

Next, an operation of the above-described training image generation device 2 will be described.

Figure 4:
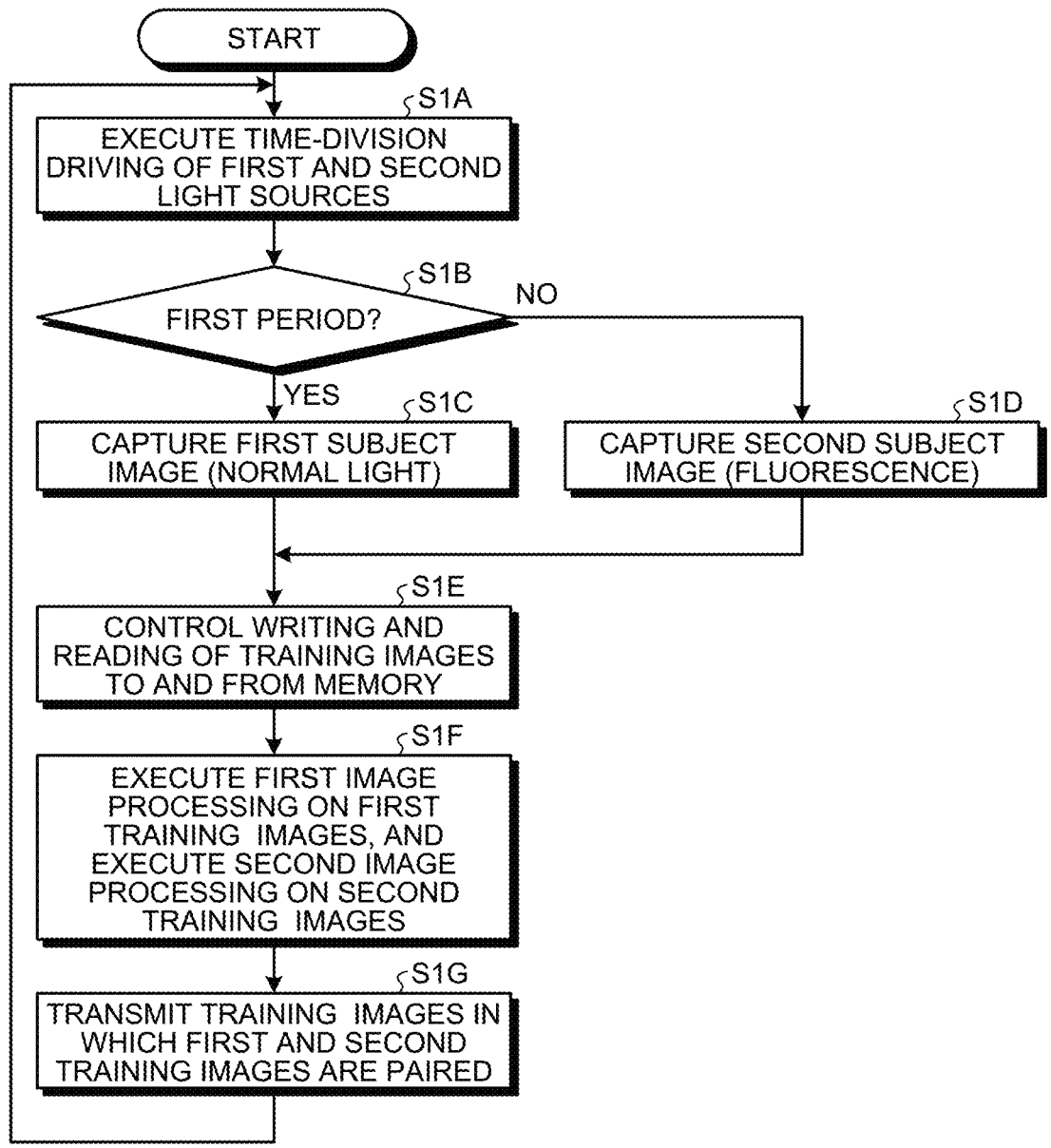
FIG. 4 is a flowchart illustrating an operation of the training image generation device.
Figure 5:
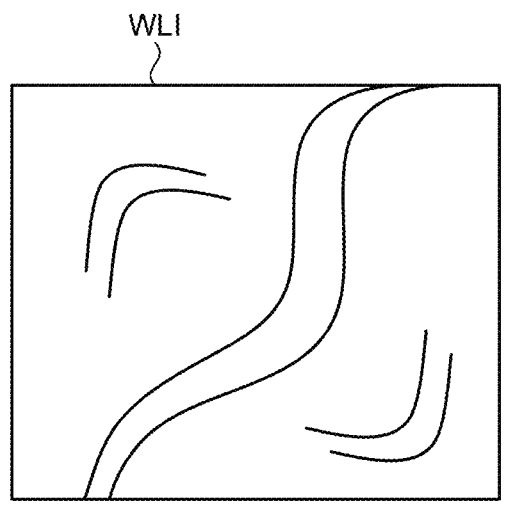
FIG. 5 is a view for describing the operation of the training image generation device.
Figure 6:
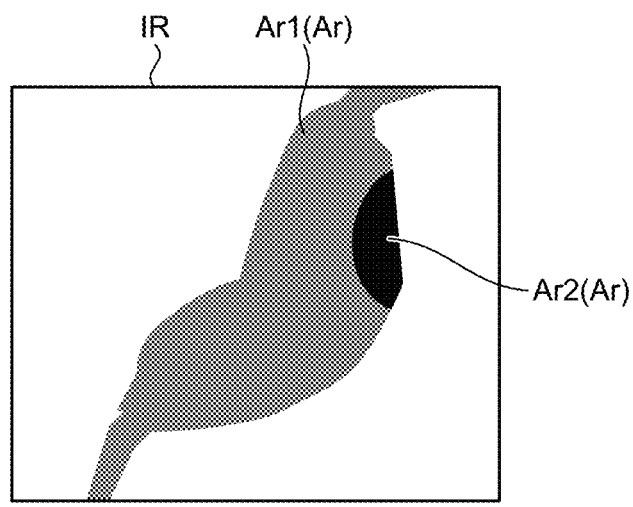
FIG. 6 is a view for describing the operation of the training image generation device.

FIG. 4 is a flowchart illustrating the operation of the training image generation device 2. FIG. 5 and FIG. 6 are views for describing the operation of the training image generation device 2. Specifically, FIG. 5 is a view illustrating a first training image WLI of one frame after execution of the first image processing. FIG. 6 is a view illustrating a second training image IR of one frame after execution of the second image processing. Note that the second training image IR illustrated in FIG. 6 is expressed in a gray scale, and intensity (corresponding to luminance value) of a component of the captured fluorescence is higher (luminance value is larger) as approaching black.

First, the control unit 284 executes time-division driving of the first and second light sources 221 and 222 (Step S1A). Specifically, in Step S1A, based on the synchronization signal, the control unit 284 causes the first light source 221 to emit the normal light (white light) in the first period and causes the second light source 222 to emit the near-infrared excitation light in the second period in the alternately repeated first and second periods.

After Step S1A, the control unit 284 causes the imaging element 242b to capture the first and second subject images in the first and second periods respectively in synchronization with the light emission timing of the first and second light sources 221 and 222 based on the synchronization signal (Steps S1B to S1D). That is, in a case of the first period (Step S1B: Yes), in other words, in a case where the normal light (white light) is emitted to the inside of the living body, the imaging element 242b captures the first subject image (normal light) and generates the first training image (Step S1C). On the other hand, in a case of the second period (Step S1B: No), in other words, in a case where the near-infrared excitation light is emitted to the inside of the living body, the imaging element 242b captures the second subject image (fluorescence) and generates the second training image (Step S1D).

After Step S1C and S1D, the memory controller 283a controls writing and reading of the training images to and from the memory 282 based on the synchronization signal (Step S1E).

After Step S1E, the first and second image processing units 283b and 283c execute the following processing (Step S1F).

That is, the first image processing unit 283b sequentially executes the first image processing on first training images sequentially read from the memory 282 by the memory controller 283a. Then, the first image processing unit 283b outputs the first training image WLI illustrated in FIG. 5, for example. On the other hand, the second image processing unit 283c sequentially executes the second image processing on second training images sequentially read from the memory 282 by the memory controller 283a. Then, the second image processing unit 283c outputs the second training image IR illustrated in FIG. 6, for example. Note that, since being images captured by the same imaging element 242b, the first and second training images have the same image size as can be seen from comparison between the first and second training images WLI and IR illustrated in FIG. 5 and FIG. 6. That is, the same pixel positions in the first and second training images are pixels acquired by imaging of the same position of the same subject.

After Step S1F, the control unit 284 controls an operation of the third communication unit 288, and sequentially transmits, to the learning device 3, training images in which the first and second training images respectively output from the first and second image processing units 283b and 283c in Step S1F are paired (Step S1G).

Then, the control unit 284 returns to Step S1A.

[3. Configuration of the Learning Device]

Next, the configuration of the learning device 3 will be described.

Figure 7:
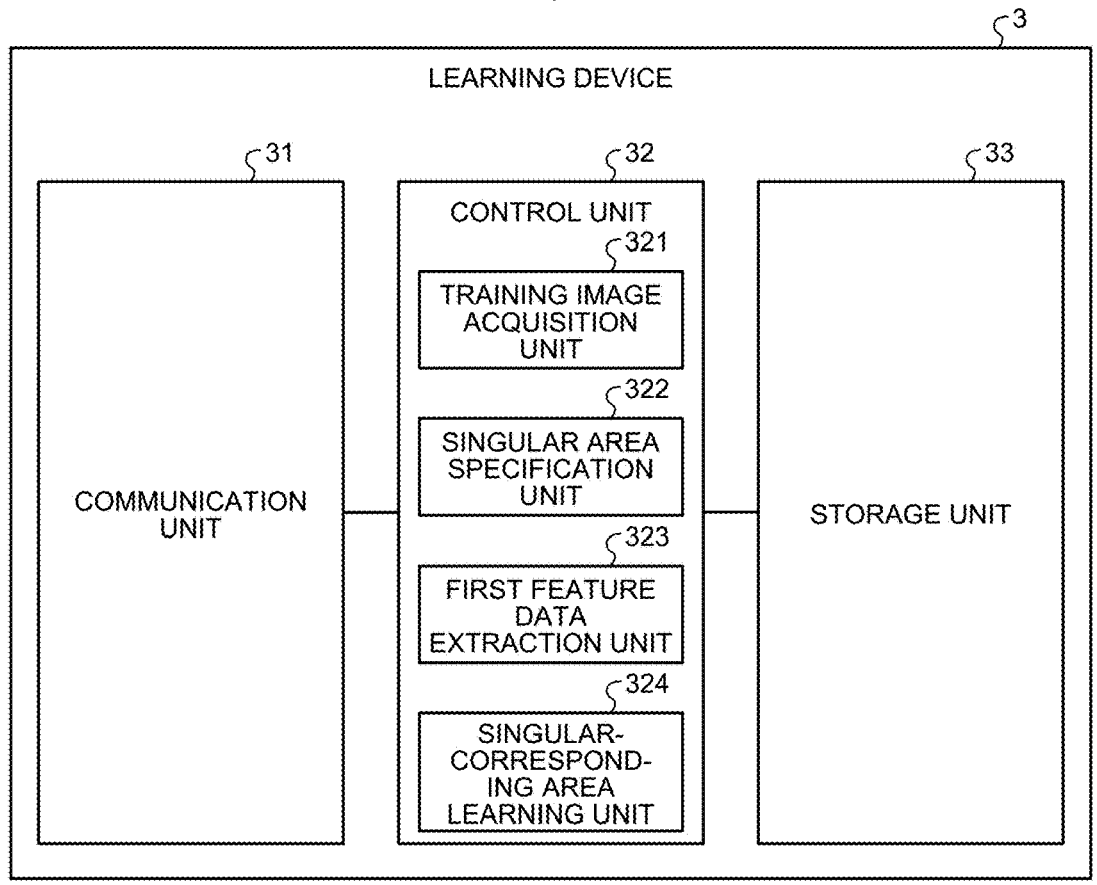
FIG. 7 is a view illustrating a configuration of a learning device.

FIG. 7 is a view illustrating the configuration of the learning device 3.

The learning device 3 is, for example, a server device, and is a portion that generates a learning model by using the training images generated by the training image generation device 2. As illustrated in FIG. 7, this learning device 3 includes a communication unit 31, a control unit 32, and a storage unit 33.

The communication unit 31 transmits/receives information to/from the training image generation device 2 (third communication unit 288) via the network NE under the control of the control unit 32.

The control unit 32 includes, for example, a CPU, an FPGA, or the like, and controls an operation of the entire learning device 3. This control unit 32 includes a training image acquisition unit 321, a singular area specification unit 322, a first feature data extraction unit 323, and a singular-corresponding area learning unit 324.

Note that functions of the training image acquisition unit 321, the singular area specification unit 322, the first feature data extraction unit 323, and the singular-corresponding area learning unit 324 will be described in "4. Operation of the learning device" described later.

The storage unit 33 stores a program executed by the control unit 32, information necessary for processing by the control unit 32, information generated by the processing, and the like.

[4. Operation of the Learning Device]

Next, the operation of the learning device 3 described above will be described.

Figure 8:
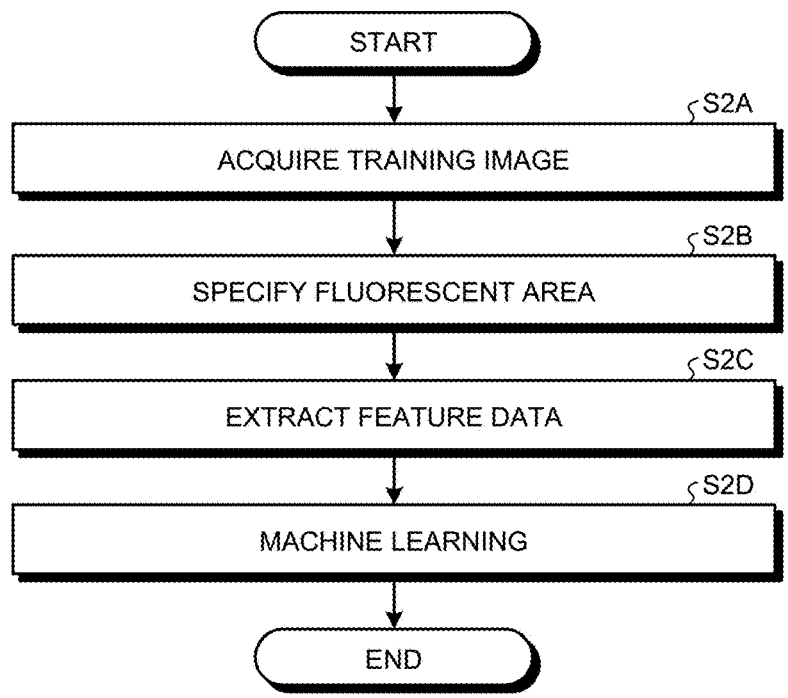
FIG. 8 is a flowchart illustrating an operation of the learning device.

FIG. 8 is a flowchart illustrating the operation of the learning device 3.

First, via the communication unit 31, the training image acquisition unit 321 sequentially acquires training images (first and second training images) transmitted from the training image generation device 2 (third communication unit 288) (Step S2A).

After Step S2A, the singular area specification unit 322 specifies a fluorescent area (singular area) in the second training image (Step S2B).

Specifically, the singular area specification unit 322 specifies, as the fluorescent area, an area in which a pixel level is equal to or higher than a specific threshold in the second training image.

Here, examples of the pixel level include a luminance value corresponding to a Y signal (luminance signal) and an RGB value (pixel value). In the present embodiment, the luminance value is employed as the pixel level. That is, in the second training image IR illustrated in FIG. 6, an area Ar in which the luminance value is equal to or larger than the specific threshold is specified as the fluorescent area. Furthermore, in the present embodiment, the singular area specification unit 322 specifies, as the fluorescent area Ar, each of a first fluorescent area (first singular area) Ar1 in which the luminance value is within a first range (gray portion illustrated in FIG. 6) and a second fluorescent area (second singular area) Ar2 in which the luminance value is within a second range higher than the first range (black portion illustrated in FIG. 6).

After Step S2B, the first feature data extraction unit 323 extracts feature data of each of a fluorescence-corresponding area (singular-corresponding area) and a non-corresponding area in the first training image paired with the second training image in which the fluorescent area is specified in Step S2B (Step S2C).

Here, in the first training image, the fluorescence-corresponding area is an area at a pixel position corresponding to the fluorescent area of the second training image (the same pixel position as the fluorescent area). Also, the non-corresponding area is an area other than the fluorescence-corresponding area in the first training image. In the present embodiment, the fluorescence-corresponding area includes, in the first training image, a first fluorescence-corresponding area at a pixel position corresponding to the first fluorescent area Ar1 of the second training image and a second fluorescence-corresponding area at a pixel position corresponding to the second fluorescent area Ar2 of the second training image. That is, the first feature data extraction unit 323 extracts feature data of each of the first and second fluorescence-corresponding areas and the non-corresponding area.

In addition, as the feature data of the first fluorescence-corresponding area, the following extraction methods (1) to (3) can be exemplified.

(1) Feature data is extracted for each pixel included in the first fluorescence-corresponding area.

(2) With a plurality of pixels included in the first fluorescence-corresponding area as one group, feature data is extracted for each group.

(3) Feature data of the entire first fluorescence-corresponding area is extracted.

Note that extraction methods for the feature data of the second fluorescence-corresponding area and the feature data of the non-corresponding area are also similar to the above.

Furthermore, examples of the feature data include feature data related to a resolution, edge, color, brightness, noise, contrast, histogram, and the like.

After Step S2C, the singular-corresponding area learning unit 324 generates a learning model by performing machine learning on the first and second fluorescence-corresponding areas based on the feature data of the first fluorescence-corresponding area, the feature data of the second fluorescence-corresponding area, and the feature data of the non-corresponding area (Step S2D). That is, by using the learning model, it is possible to determine whether an area having the feature data is any of the first and second fluorescence-corresponding areas and the non-corresponding area from the feature data.

Here, examples of the machine learning include machine learning using a convolutional neural network (deep learning). That is, in the machine learning, as the number of training images in which the first and second training images are paired increases, it becomes possible to generate a learning model capable of more accurately determining the first and second fluorescence-corresponding areas and the non-corresponding area.

In the present embodiment, when generating the learning model by performing the machine learning on the first and second fluorescence-corresponding areas, the singular-corresponding area learning unit 324 sets a weight of feature data related to a blue color component to be lower than a weight of feature data related to the other red and green color components. For example, the feature data related to the blue color component is not used for the machine learning.

Then, the singular-corresponding area learning unit 324 stores the generated learning model in the storage unit 33.

[5. Configuration of the Medical Observation Device]

Next, a medical observation device 4 that estimates a fluorescent area by using the learning model generated by the learning device 3 will be described.

Figure 9:
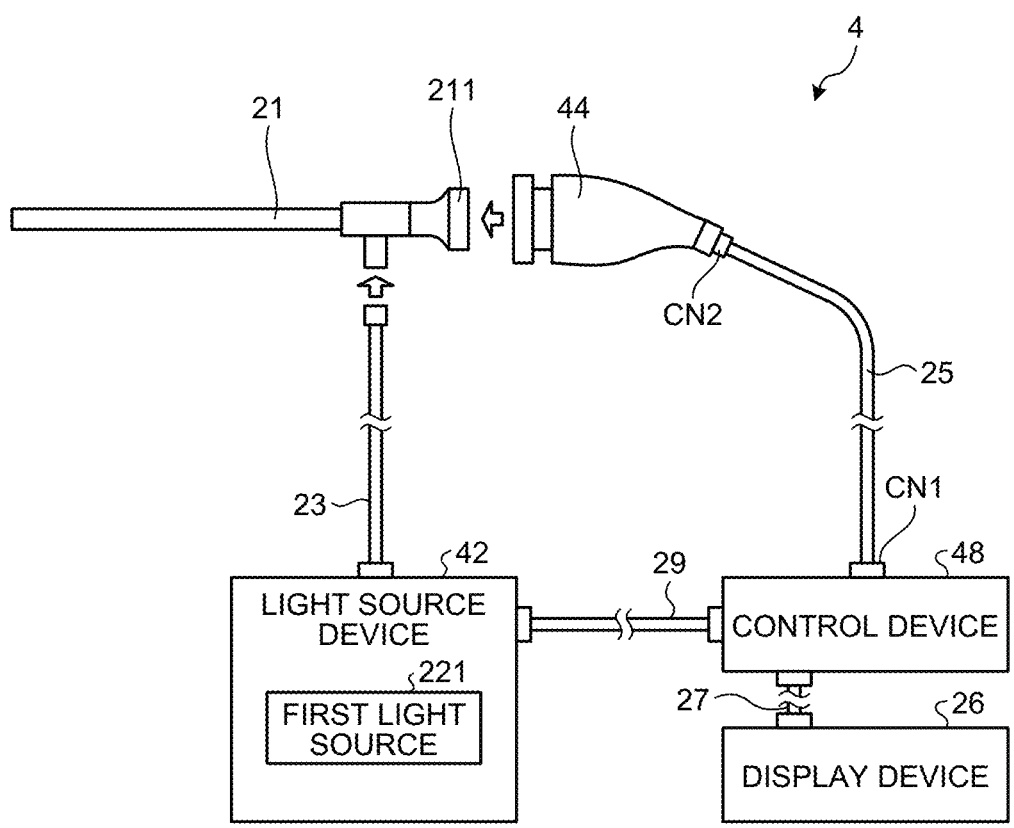
FIG. 9 is a view illustrating a configuration of a medical observation device.
Figure 10:
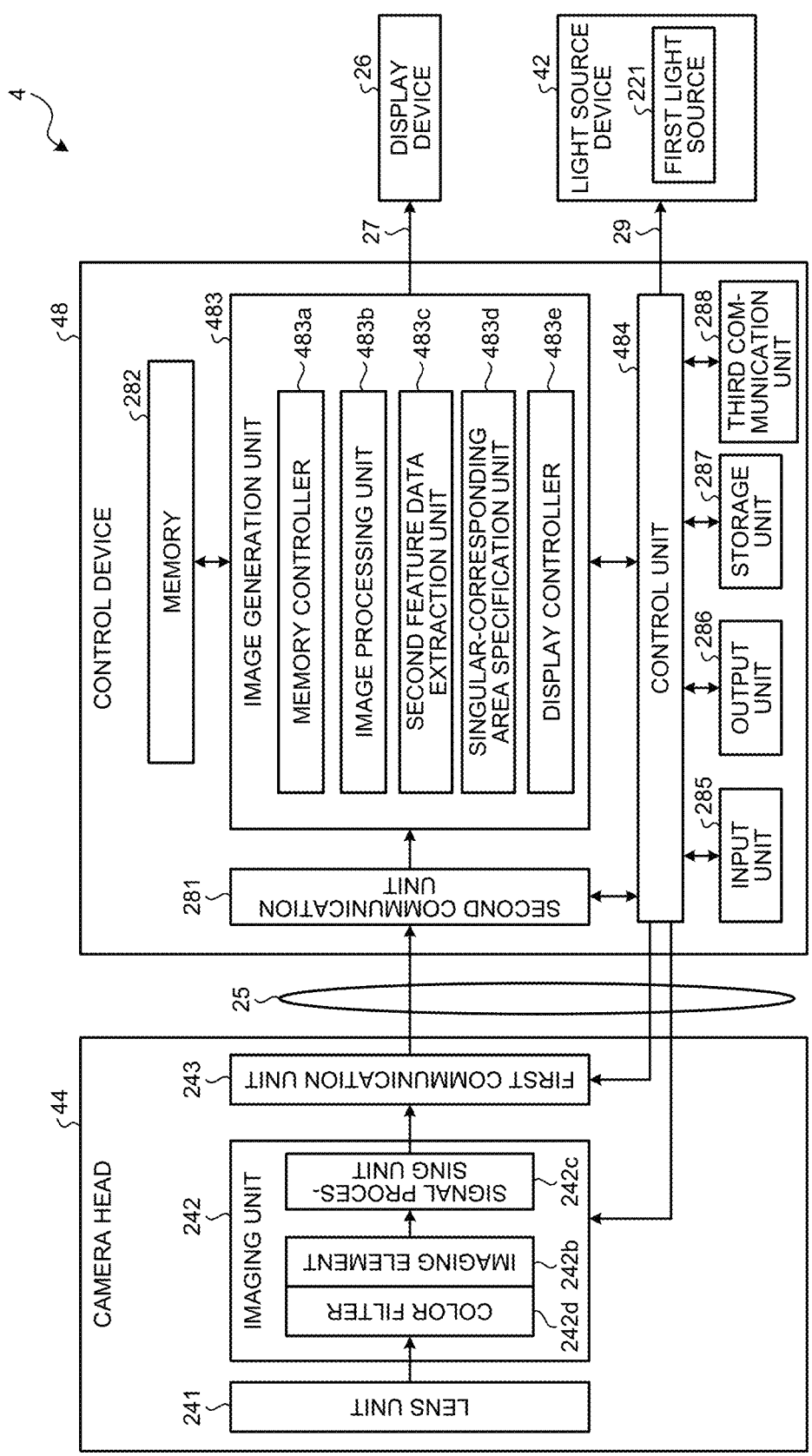
FIG. 10 is a view illustrating configurations of a camera head and a control device.

FIG. 9 is a view illustrating the configuration of the medical observation device 4. FIG. 10 is a view illustrating configurations of a camera head 44 and a control device 48.

As illustrated in FIG. 9 or FIG. 10, the medical observation device 4 has a configuration substantially similar to that of the training image generation device 2. Note that the same reference sign is assigned to a configuration, which is the same as that of the training image generation device 2, in the medical observation device 4.

In the following, among configurations of the medical observation device 4, configurations different from those of the training image generation device 2 will be mainly described.

In the medical observation device 4, the light source device 42 has a configuration corresponding to the light source device 22 in the training image generation device 2. As illustrated in FIG. 9 or FIG. 10, this light source device 42 includes only a first light source 221. That is, unlike the light source device 22, the light source device 42 does not include a second light source 222.

Then, in the light source device 42, the first light source 221 is driven and emits only the normal light (white light) under the control of the control device 48.

Note that although the light source device 42 is configured separately from the control device 48 in the present embodiment, this is not a limitation, and a configuration provided inside the control device 48 may be employed.

In the medical observation device 4, the camera head 44 has a configuration corresponding to the camera head 24 in the training image generation device 2. As illustrated in FIG. 10, since the light source device 42 does not include the second light source 222, this camera head 44 has a configuration in which the excitation light cut-off filter 242*a* is omitted from the camera head 24.

Then, the camera head 44 (imaging element 242*b*) performs imaging in a specific frame period under the control of the control device 48. Hereinafter, for distinction from the first training image, an image generated by capturing the first subject image (normal light) by the camera head 44 (imaging element 242*b*) will be referred as a captured image.

The control device 48 corresponds to the medical image processing device according to the present disclosure. In the medical observation device 4, this control device 48 has a configuration corresponding to the control device 28 in the training image generation device 2. In this control device 48, as illustrated in FIG. 10, an image generation unit 483 and a control unit 484 are employed with respect to the control device 28 instead of the image generation unit 283 and the control unit 284.

The image generation unit 483 processes captured images (RAW signals (digital signals)) sequentially output from the camera head 44 (first communication unit 243) and received by the second communication unit 281 under the control of the control unit 484. As illustrated in FIG. 10, this image generation unit 483 includes a memory controller 483*a*, an image processing unit 483*b*, a second feature data extraction unit 483*c*, a singular-corresponding area specification unit 483*d*, and a display controller 483*e*.

Note that functions of the memory controller 483*a*, the image processing unit 483*b*, the second feature data extraction unit 483*c*, the singular-corresponding area specification unit 483*d*, and the display controller 483*e* will be described in "6. Operation of the medical observation device" described later.

The control unit 484 includes, for example, a CPU, an FPGA, or the like, and controls operations of the light source device 42, the camera head 44, and the display device 26 and controls an operation of the entire control device 48 by outputting a control signal through the first to third transmission cables 25, 27, and 29.

Note that a part of the function of the control unit 484 will be described in "6. Operation of the medical observation device" described later.

[6. Operation of the Medical Observation Device]

Next, an operation of the medical observation device 4 described above will be described.

Figure 11:
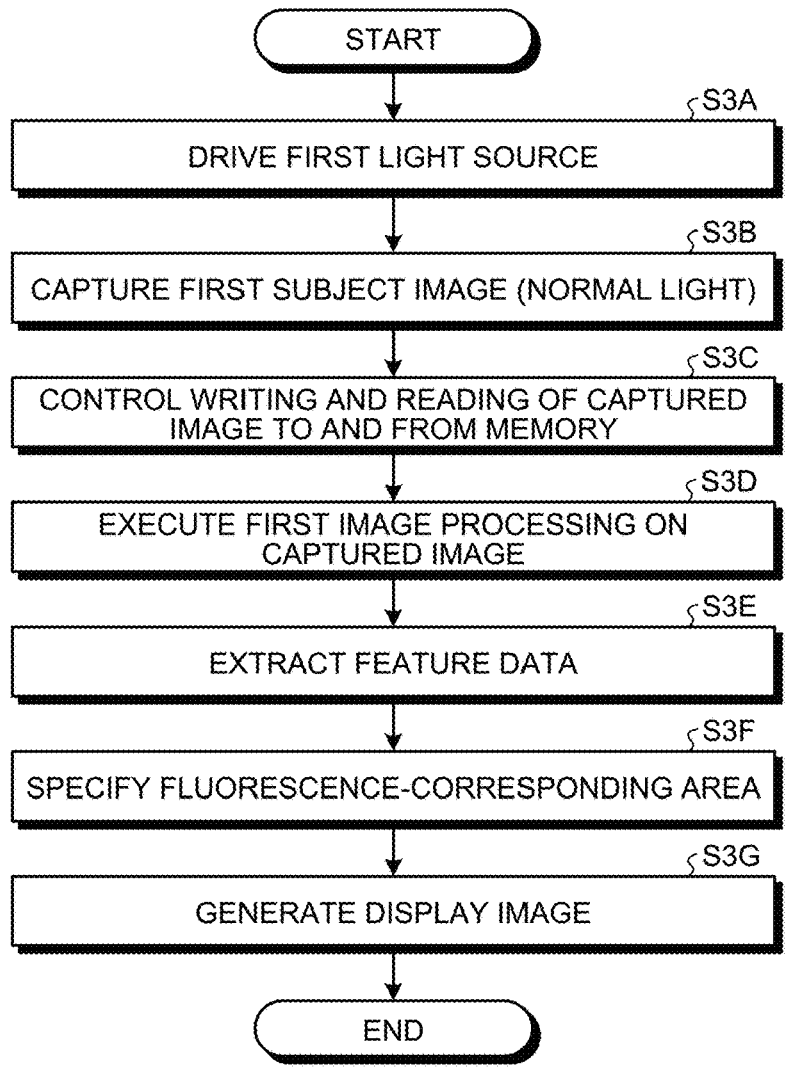
FIG. 11 is a flowchart illustrating an operation of the medical observation device.
Figure 12:
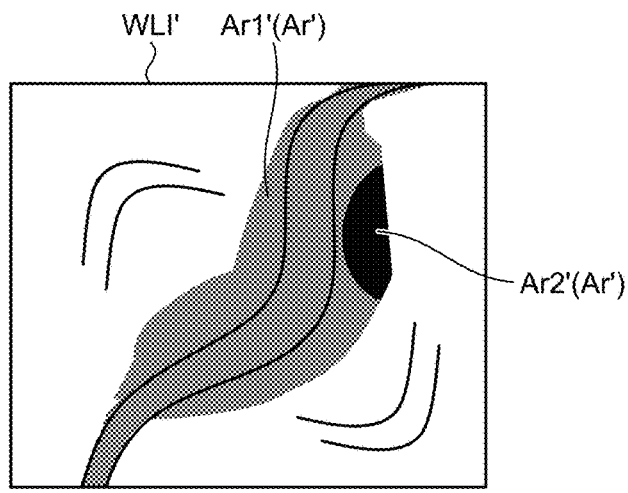
FIG. 12 is a view for describing the operation of the medical observation device.

FIG. 11 is a flowchart illustrating the operation of the medical observation device 4. FIG. 12 is a view for describing the operation of the medical observation device 4. Specifically, FIG. 12 is a view illustrating a display image WLI' generated in Step S3G. Here, in FIG. 12, for convenience of description, it is assumed that a captured image that is the same as the first training image WLI illustrated in FIG. 5 is generated in Step S3B.

Note that it is assumed that the control unit 484 controls an operation of the third communication unit 288, receives a learning model from the learning device 3, and stores the learning model in the storage unit 287 before executing the operation of the medical observation device 4 described in the following.

First, the control unit 484 drives the light source device 42 (first light source 221) (Step S3A). As a result, the normal light (white light) is emitted to the inside of the living body (observation target).

After Step S3A, the control unit 484 generates a captured image by causing the imaging element 242*b* to capture the first subject image (normal light) in a specific frame period (Step S3B).

After Step S3B, the memory controller 483*a* controls writing and reading of the captured image to and from the memory 282 (Step S3C). Specifically, the memory controller 483*a* sequentially writes, into the memory 282, captured images sequentially output from the camera head 44 (first communication unit 243) and received by the second communication unit 281. In addition, the memory controller 483*a* reads the captured images from the memory 282 at timing of specification, and causes the image processing unit 483*b* to input the read captured images.

After Step S3C, the image processing unit 483*b* sequentially executes the above-described first image processing on each of the captured images sequentially read from the memory 282 by the memory controller 483*a* (Step S3D).

After Step S3D, with respect to the captured images sequentially output from the image processing unit 483*b* in Step S3D, the second feature data extraction unit 483*c* extracts feature data of each area of the captured images (Step S3E).

Here, as the feature data, the following extraction methods (4) and (5) can be exemplified.

(4) Feature data is extracted for each pixel included in a captured image.

(5) With a plurality of pixels included in a captured image as one group (area), feature data is extracted for each group.

In addition, the feature data extracted by the second feature data extraction unit 483*c* is the same kind of feature data as the feature data extracted by the first feature data extraction unit 323.

After Step S3E, based on the feature data extracted in Step S3E, the singular-corresponding area specification unit 483*d* specifies the first and second fluorescence-corresponding areas in the captured images by using the learning model stored in the storage unit 287 (Step S3F).

After Step S3F, the display controller 483*e* generates a display image in which the first and second fluorescence-corresponding areas specified in Step S3F are displayed in a manner of being distinguished from the other area in the captured images (Step S3G). For example, in a case where it is assumed that a captured image that is the same as the first training image WLI illustrated in FIG. 5 is generated in Step S3B, a display image WLI' in which first and second fluorescence-corresponding areas Ar1' and Ar2' (fluorescence-corresponding areas Ar') are distinguished from the other area is generated in the captured image, as illustrated in FIG. 12. As a method of the distinction, for example, application of a single color (such as green) to the fluorescence-corresponding areas Ar' in the captured image can be exemplified. In addition, as described above, the second fluorescent area Ar2 is an area having the luminance value larger than that of the first fluorescent area Ar1. Thus, it is preferable that a color darker than that of the first fluorescence-corresponding area Ar1' (expressed in gray in FIG. 12, for convenience of description) is applied to the second fluorescence-corresponding area Ar2' (expressed in black in FIG. 12, for convenience of description).

Then, the display controller 483e generates a video signal corresponding to the display image WLI', and outputs the video signal to the display device 26 through the second transmission cable 27. As a result, the display device 26 displays the display image WLI'.

According to the present embodiment described above, the following effects are acquired.

The learning device 3 according to the present embodiment uses the training images in which the first and second training images are paired, and generates the learning model by performing, based on the feature data of the fluorescence-corresponding area at the pixel position corresponding to the fluorescent area in the second training image in the first training image, machine learning on the fluorescence-corresponding area.

Then, the control device 48 according to the present embodiment acquires the captured image acquired by capturing the first subject image (normal light) from the inside of the living body (observation target), and specifies the fluorescence-corresponding area in the captured image by using the above-described learning model based on the feature data of each area in the captured image.

That is, since the fluorescent area can be estimated by utilization of the learning model, it is not necessary to administer a fluorescent substance such as indocyanine green into the living body. Thus, convenience can be improved.

In addition, in the medical observation device 4, the second light source 222 and the excitation light cut-off filter 242a can be omitted since it is not necessary to emit near-infrared excitation light to the inside of the living body. Thus, the configuration can be simplified and downsized.

In addition, in the learning device 3 according to the present embodiment, the fluorescent area is divided into two stages of the first and second fluorescence areas according to levels of the luminance values. The same applies to a fluorescence-corresponding area corresponding to the fluorescent area. That is, the fluorescence-corresponding area specified by the control device 48 is also divided into the first and second fluorescence-corresponding areas. For this reason, the user such as a doctor can easily recognize a portion in which the intensity of the fluorescent component is estimated to be high and a portion in which the intensity of the fluorescent component is estimated to be low from the display image.

Incidentally, when a lesion such as cancer is specified by image recognition, it is not necessary to consider the feature data of the blue color component.

In the learning device 3 according to the present embodiment, when the learning model is generated by machine learning on the fluorescence-corresponding area, the weight of the feature data related to the blue color component is made lower than the weight of the feature data related to other color components. For example, the feature data related to the blue color component is not used for the machine learning. Thus, a processing load can be reduced since machine learning can be performed without consideration of unnecessary feature data.

Other Embodiments

Although modes for carrying out the present disclosure have been described above, the present disclosure is not limited only to the above-described embodiment.

Although the fluorescent area is divided into two stages of the first and second fluorescence areas according to the levels of the luminance values in the above-described embodiment, this is not a limitation. There may be only one fluorescent area, or the fluorescent area may be divided into three stages or more according to the levels of the luminance values. The same applies to the fluorescence-corresponding area corresponding to the fluorescent area.

In the above-described embodiment, the light in the first wavelength band is the normal light (white light), and the light in the second wavelength band is the near-infrared excitation light. However, this is not a limitation. As long as the first wavelength band and the second wavelength band are different, other light may be employed. At this time, the first and second wavelength bands may be partially overlapping bands, or may be bands that do not overlap at all.

For example, narrowband light used in so-called narrow band imaging (NBI) may be employed as the light in the second wavelength band. At this time, the light in the first wavelength band may be the normal light (white light) or other light.

Incidentally, photo dynamic diagnosis (PDD) that is one of cancer diagnosis methods for detecting a cancer cell is conventionally known.

In the photo dynamic diagnosis, for example, a photosensitive substance such as a 5-aminolevulinic acid (hereinafter, referred to as 5-ALA) is used. The 5-ALA is a natural amino acid originally included in living bodies of animals and plants. This 5-ALA is taken into cells after administration into a body, and is biosynthesized into protoporphyrin in mitochondria. The protoporphyrin is excessively accumulated in the cancer cell. In addition, the protoporphyrin that is excessively accumulated in the cancer cell has photoactivity. Thus, when being excited by excitation light (such as blue visible light in a wavelength band of 375 nm to 445 nm), the protoporphyrin emits fluorescence (such as red fluorescence in a wavelength band of 600 nm to 740 nm). As described above, a cancer diagnostic method of causing the cancer cell to fluorescently emit light by using the photosensitive substance is called the photo dynamic diagnosis.

Then, in the above-described embodiment, the excitation light that excites the protoporphyrin (such as blue visible light in the wavelength band of 375 nm to 445 nm) may be employed as the light in the second wavelength band. At this time, the light in the first wavelength band may be the normal light (white light) or other light.

Although the first and second training images are generated by the single imaging element 242b in the above-described embodiment, this is not a limitation. For example, a configuration in which a first subject image and a second subject image are separated and respectively captured by two imaging elements and first and second training images are respectively generated by the two imaging elements may be employed. At this time, the learning device 3 needs to recognize a correspondence relationship of pixels between the first and second training images.

Although the training image generation device 2 and the learning device 3 are communicably connected to each other via the network NE in the above-described embodiment, this is not a limitation. The training image generation device 2 and the learning device 3 may be configured as one device.

Although the medical image processing device according to the present disclosure is mounted on the medical observation device 4 in which the insertion unit 21 includes a rigid endoscope in the above-described embodiment, this is not a limitation. For example, the medical image processing device according to the present disclosure may be mounted on a medical observation device in which an insertion unit 21 includes a flexible endoscope. In addition, the medical image processing device according to the present disclosure may be mounted on a medical observation device such as a surgical microscope that enlarges and observes a predetermined visual field area inside a subject (inside a living body) or a subject surface (living body surface) (see, for example, Japanese Patent Application Laid-open No. 2016-42981).

In the above-described embodiment, a part of the configuration of the camera head 44 or a part of the configuration of the control device 48 may be provided in, for example, the connector CN1 or the connector CN2.

Note that the following configurations also belong to the technical scope of the present disclosure.

(1) A learning device including:
a training image acquisition unit configured to acquire training images in which a first training image acquired by capturing light from a subject irradiated with light in a first wavelength band and a second training image acquired by capturing light from the subject irradiated with light in a second wavelength band different from the first wavelength band are paired;
a singular area specification unit configured to specify a singular area in the second training image;
a first feature data extraction unit configured to extract feature data of a singular-corresponding area at a pixel position, the pixel position corresponding to the singular area in the first training image; and
a singular-corresponding area learning unit configured to generate a learning model by performing machine learning on the singular-corresponding area based on the feature data.

(2) The learning device according to (1), wherein
the subject emits fluorescence by being irradiated with excitation light in the second wavelength band,
the second training image is acquired by capturing the fluorescence from the subject irradiated with the excitation light, and
the singular area specification unit is configured to specify, as the singular area, an area in which intensity of a component of the fluorescence is equal to or higher than a specific threshold in the second training image.

(3) The learning device according to (1) or (2), wherein the singular area specification unit is configured to specify, as the singular area, an area in which a pixel level is equal to or higher than a specific threshold in the second training image.

(4) The learning device according to (3), wherein
the singular area specification unit is configured to specify, as the singular area, each of a first singular area in which the pixel level is within a first range and a second singular area in which the pixel level is within a second range higher than the first range,
the first feature data extraction unit is configured to extract feature data of each of a first singular-corresponding area, which is the singular-corresponding area in the first training image and is at a pixel position corresponding to the first singular area, and a second singular-corresponding area which is the singular-corresponding area in the first training image and is at a pixel position corresponding to the second singular area, and
the singular-corresponding area learning unit is configured to perform machine learning on each of the first singular-corresponding area and the second singular-corresponding area based on the feature data.

(5) The learning device according to any one of (1) to (4), wherein
the feature data includes feature data related to at least one of color and luminance, and
the singular-corresponding area learning unit is configured to make a weight of the feature data related to a blue color component lower than a weight of the feature data related to another color component when performing the machine learning on the singular-correspondence area and generating a learning model.

(6) The learning device according to any one of (1) to (5), wherein
the light in the first wavelength band is emitted in a first period of the first period and a second period that are alternately repeated, and
the light in the second wavelength band is emitted in the second period.

(7) A medical image processing device including:
a captured image acquisition unit configured to acquire a captured image acquired by capturing light from an observation target irradiated with light in a first wavelength band;
a second feature data extraction unit configured to extract feature data of each area of the captured image; and
a singular-corresponding area specification unit configured to specify a singular-corresponding area in the captured image by using a learning model constructed by machine learning based on the feature data, wherein
the learning model is generated by the machine learning on the singular-corresponding area by utilization of training images, in which a first training image acquired by capturing light from a subject irradiated with the light in the first wavelength band and a second training image acquired by capturing light from the subject irradiated with light in a second wavelength band different from the first wavelength band are paired, based on the feature data of the singular-corresponding area at a pixel position, the pixel position corresponding to a singular area in the second training image, in the first training image.

(8) The medical image processing device according to (7), wherein
the subject emits fluorescence by being irradiated with excitation light in the second wavelength band,
the second training image is acquired by capturing the fluorescence from the subject irradiated with the excitation light, and
the singular area is an area in which intensity of a component of the fluorescence is equal to or higher than a specific threshold in the second training image.

(9) The medical image processing device according to (7) or (8), wherein the singular area is an area in which a pixel level is equal to or larger than a specific threshold in the second training image.

(10) The medical image processing device according to (9), wherein
the singular area includes a first singular area in which the pixel level is within a first range, and a second singular area in which the pixel level is within a second range higher than the first range, and the learning model is generated by machine learning on each of a first singular-corresponding area, which is the singular-corresponding area in the first training image and is at a pixel position corresponding to the first singular area, and a second singular-corresponding area, which is the singular-corresponding area in the first training image and is at a pixel position corresponding to the second singular area, based on the feature data of the first singular-corresponding area and the second singular-corresponding area.

(11) The medical image processing device according to any one of (7) to (10), wherein the feature data includes feature data related to at least one of color and luminance, and the learning model is generated by machine learning on the singular-corresponding area in a state in which a weight of the feature data related to a blue color component is made lower than a weight of the feature data related to another color component.

(12) The medical image processing device according to any one of (7) to (11), wherein the light in the first wavelength band is emitted in a first period of the first period and a second period that are alternately repeated, and the light in the second wavelength band is emitted in the second period.

(13) The medical image processing device according to any one of (7) to (12), further including a display controller configured to generate a display image in which the singular-corresponding area is displayed in a manner of being distinguished from another area in the captured image.

REFERENCE SIGNS LIST

1 LEARNING SYSTEM
2 TRAINING IMAGE GENERATION DEVICE
3 LEARNING DEVICE
4 MEDICAL OBSERVATION DEVICE
21 INSERTION UNIT
22, 42 LIGHT SOURCE DEVICE
23 LIGHT GUIDE
24, 44 CAMERA HEAD
25 FIRST TRANSMISSION CABLE
26 DISPLAY DEVICE
27 SECOND TRANSMISSION CABLE
28, 48 CONTROL DEVICE
29 THIRD TRANSMISSION CABLE
31 COMMUNICATION UNIT
32 CONTROL UNIT
33 STORAGE UNIT
211 EYEPIECE
221 FIRST LIGHT SOURCE
222 SECOND LIGHT SOURCE
241 LENS UNIT
242 IMAGING UNIT
242a EXCITATION LIGHT CUT-OFF FILTER
242b IMAGING ELEMENT
242c SIGNAL PROCESSING UNIT
242d COLOR FILTER
243 FIRST COMMUNICATION UNIT
281 SECOND COMMUNICATION UNIT
282 MEMORY
283 IMAGE GENERATION UNIT
283a MEMORY CONTROLLER
283b FIRST IMAGE PROCESSING UNIT
283c SECOND IMAGE PROCESSING UNIT
283d DISPLAY CONTROLLER
284, 484 CONTROL UNIT
285 INPUT UNIT
286 OUTPUT UNIT
287 STORAGE UNIT
288 THIRD COMMUNICATION UNIT
321 TRAINING IMAGE ACQUISITION UNIT
322 SINGULAR AREA SPECIFICATION UNIT
323 FIRST FEATURE DATA EXTRACTION UNIT
324 SINGULAR-CORRESPONDING AREA LEARNING UNIT
483 IMAGE GENERATION UNIT
483a MEMORY CONTROLLER
483b IMAGE PROCESSING UNIT
483c SECOND FEATURE DATA EXTRACTION UNIT
483d SINGULAR-CORRESPONDING AREA SPECIFICATION UNIT
483e DISPLAY CONTROLLER
Ar FLUORESCENT AREA
Ar' FLUORESCENCE-CORRESPONDING AREA
Ar1 FIRST FLUORESCENT AREA
Ar1' FIRST FLUORESCENCE-CORRESPONDING AREA
Ar2 SECOND FLUORESCENT AREA
Ar2' SECOND FLUORESCENCE-CORRESPONDING AREA
CN1, CN2 CONNECTOR
IR SECOND TRAINING IMAGE
NE NETWORK
WLI FIRST TRAINING IMAGE
WLI' DISPLAY IMAGE

The invention claimed is:

1. A learning device comprising:

circuitry configured to acquire training images in which a first training image acquired by capturing light from a subject irradiated with light in a first wavelength band and a second training image acquired by capturing light from the subject irradiated with light in a second wavelength band different from the first wavelength band are paired;

specify a singular area in the second training image, wherein the singular area is an area in which a pixel level is equal to or larger than a specific threshold in the second training image, the singular area includes a first singular area in which the pixel level is within a first range each of a first singular area in which the pixel level is within a first range and a second singular area in which the pixel level is within a second range higher than the first range;

extract feature data of each of a first singular-corresponding area, which is the singular-corresponding area in the first training image and is at a pixel position corresponding to the first singular area, and a second singular-corresponding area, which is the singular-corresponding area in the first training image and is at a pixel position corresponding to the second singular area, specified in the second training image; and generate a learning model by performing machine learning on the first singular-corresponding area and the second singular-corresponding area based on the feature data.

2. The learning device according to claim 1, wherein the subject emits fluorescence by being irradiated with excitation light in the second wavelength band, the second training image is acquired by capturing the fluorescence from the subject irradiated with the excitation light, and the circuitry is configured to specify, as the singular area, an area in which intensity of a component of the fluorescence is equal to or higher than a specific threshold in the second training image.

3. A learning device comprising:

circuitry configured to acquire training images in which a first training image acquired by capturing light from a subject irradiated with light in a first wavelength band and a second training image acquired by capturing light from the subject irradiated with light in a second wavelength band different from the first wavelength band are paired;

specify a singular area in the second training image;

extract feature data of a singular-corresponding area at a pixel position in the first training image, the pixel position corresponding to the singular area in specified in the second training image; and generate a learning model by performing machine learning on the singular-corresponding area based on the feature data, wherein the feature data includes feature data related to at least one of color and luminance, and the circuitry is configured to make a weight of the feature data related to a blue color component lower than a weight of the feature data related to another color component when performing the machine learning on the singular-correspondence area and generating a learning model.

4. The learning device according to claim 1, wherein the light in the first wavelength band is emitted in a first period of the first period and a second period that are alternately repeated, and the light in the second wavelength band is emitted in the second period.

5. A medical image processing device comprising:

circuitry configured to acquire a captured image acquired by capturing light from an observation target irradiated with light in a first wavelength band;

extract feature data of each area of the captured image; and specify a singular-corresponding area in the captured image by using a learning model constructed by machine learning based on the feature data, wherein the learning model is generated by the machine learning on the singular-corresponding area by utilization of training images, in which a first training image acquired by capturing light from a subject irradiated with the light in the first wavelength band and a second training image acquired by capturing light from the subject irradiated with light in a second wavelength band different from the first wavelength band are paired, based on the feature data of the singular-corresponding area at a pixel position, the pixel position corresponding to a singular area in the second training image, in the first training image, wherein the singular area is an area in which a pixel level is equal to or larger than a specific threshold in the second training image, the singular area includes a first singular area in which the pixel level is within a first range, and a second singular area in which the pixel level is within a second range higher than the first range, and the learning model is generated by machine learning on each of a first singular-corresponding area, which is the singular-corresponding area in the first training image and is at a pixel position corresponding to the first singular area, and a second singular-corresponding area, which is the singular-corresponding area in the first training image and is at a pixel position corresponding to the second singular area, based on the feature data of the first singular-corresponding area and the second singular-corresponding area.

6. The medical image processing device according to claim 5, wherein the subject emits fluorescence by being irradiated with excitation light in the second wavelength band, the second training image is acquired by capturing the fluorescence from the subject irradiated with the excitation light, and the singular area is an area in which intensity of a component of the fluorescence is equal to or higher than a specific threshold in the second training image.

7. A medical image processing device comprising:

circuitry configured to acquire a captured image acquired by capturing light from an observation target irradiated with light in a first wavelength band;

extract feature data of each area of the captured image; and specify a singular-corresponding area in the captured image by using a learning model constructed by machine learning based on the feature data, wherein the learning model is generated by the machine learning on the singular-corresponding area by utilization of training images, in which a first training image acquired by capturing light from a subject irradiated with the light in the first wavelength band and a second training image acquired by capturing light from the subject irradiated with light in a second wavelength band different from the first wavelength band are paired, based on the feature data of the singular-corresponding area at a pixel position, the pixel position corresponding to a singular area in the second training image, in the first training image, wherein the feature data includes feature data related to at least one of color and luminance, and the learning model is generated by machine learning on the singular-corresponding area in a state in which a weight of the feature data related to a blue color component is made lower than a weight of the feature data related to another color component.

8. The medical image processing device according to claim 5, wherein the light in the first wavelength band is emitted in a first period of the first period and a second period that are alternately repeated, and the light in the second wavelength band is emitted in the second period.

9. The medical image processing device according to claim 5, further comprising a display control circuit configured to generate a display image in which the singular-corresponding area is displayed in a manner of being distinguished from another area in the captured image.

10. A learning method comprising:

acquiring training images in which a first training image acquired by capturing light from a subject irradiated with light in a first wavelength band and a second training image acquired by capturing light from the subject irradiated with light in a second wavelength band different from the first wavelength band are paired;

specifying a singular area in the second training image, wherein the singular area is an area in which a pixel level is equal to or larger than a specific threshold in the second training image, the singular area includes a first singular area in which the pixel level is within a first range each of a first singular area in which the pixel level is within a first range and a second singular area in which the pixel level is within a second range higher than the first range;

extracting feature data of each of a first singular-corresponding area, which is the singular-corresponding area in the first training image and is at a pixel position corresponding to the first singular area, and a second singular-corresponding area, which is the singular-corresponding area in the first training image and is at a pixel position corresponding to the second singular area, specified in the second training image; and generating a learning model by performing machine learning on the first singular-corresponding area and the second singular-corresponding area based on the feature data.

11. The learning method according to claim 10, wherein the subject emits fluorescence by being irradiated with excitation light in the second wavelength band, the second training image is acquired by capturing the fluorescence from the subject irradiated with the excitation light, and specify, as the singular area, an area in which intensity of a component of the fluorescence is equal to or higher than a specific threshold in the second training image.

12. A learning method comprising:

acquiring training images in which a first training image acquired by capturing light from a subject irradiated with light in a first wavelength band and a second training image acquired by capturing light from the subject irradiated with light in a second wavelength band different from the first wavelength band are paired;

specifying a singular area in the second training image;

extracting feature data of a singular-corresponding area at a pixel position in the first training image, the pixel position corresponding to the singular area in specified in the second training image; and generating a learning model by performing machine learning on the singular-corresponding area based on the feature data, wherein
the feature data includes feature data related to at least one of color and luminance, and
the method further comprises setting a weight of the feature data related to a blue color component lower than a weight of the feature data related to another color component when performing the machine learning on the singular-correspondence area and generating a learning model.

13. The learning method according to claim 10, wherein the light in the first wavelength band is emitted in a first period of the first period and a second period that are alternately repeated, and the light in the second wavelength band is emitted in the second period.

* * * * *